United States Patent

Atwal

[11] Patent Number: 4,728,652
[45] Date of Patent: Mar. 1, 1988

[54] 2-SUBSTITUTED THIO OR OXY-4-ARYL OR HETEROCYCLO-5-CARBOXY-1,4-DIHYDROPYRIMIDINES, COMPOSITION CONTAINING THEM, AND METHOD OF USING THEM TO REDUCE BLOOD PRESSURE

[75] Inventor: Karnail Atwal, Cranbury, N.J.

[73] Assignee: E. R. Squibb & Sons, Inc., Princeton, N.J.

[21] Appl. No.: 854,201

[22] Filed: Apr. 21, 1986

Related U.S. Application Data

[63] Continuation-in-part of Ser. No. 736,151, May 20, 1985, abandoned.

[51] Int. Cl.$^4$ .................. A61K 31/505; A61K 31/55; C07D 239/22; C07D 417/14
[52] U.S. Cl. ..................... 514/274; 514/212; 514/223; 514/228; 514/234; 514/236; 514/252; 540/601; 544/58.1; 544/58.4; 544/58.6; 544/82; 544/121; 544/122; 544/123; 544/315; 544/316; 544/318
[58] Field of Search .............. 544/315, 316, 318, 58.1, 544/58.4, 58.6, 82, 121, 122, 123; 514/274, 212, 223, 228, 234, 236, 252; 540/601

[56] References Cited

U.S. PATENT DOCUMENTS

| | | | |
|---|---|---|---|
| 3,488,359 | 1/1970 | Bossert et al. | 514/356 |
| 4,048,171 | 9/1977 | Bossert et al. | 514/356 |
| 4,532,248 | 7/1985 | Franckowiak et al. | 514/302 |
| 4,609,494 | 9/1986 | Baldwin et al. | 544/250 |
| 4,640,922 | 2/1987 | Cho et al. | 514/256 |
| 4,675,321 | 6/1987 | Baldwin et al. | 514/274 |
| 4,683,234 | 7/1987 | Cho et al. | 514/256 |
| 4,684,655 | 8/1987 | Atwal | 514/274 |
| 4,684,656 | 8/1987 | Atwal | 514/274 |
| 4,689,414 | 8/1987 | Atwal | 544/297 |

FOREIGN PATENT DOCUMENTS 3234684 3/1984 Fed. Rep. of Germany ...... 546/321

OTHER PUBLICATIONS

*Medicinal Chemistry,* Burger edit., 2nd ed., 1960, pp. 565–571, 579–581, 600, and 601.
Merck Index, 10th Edition, 6374, Nifedipine.
Iwanami et al., Chem. Abst., vol. 86, 43570d (1977).
Zidermane et al., Chem. Abst., vol. 75, 47266e.
Goerlitzer et al., Chem. Abst., vol. 96, 8550lu (1982).
Stoltefuss et al., Chem. Abst., vol. 101, 55110v (1984).
Goerlitzer et al., Arch. Pharm. 314, 938–949 (1981).

*Primary Examiner*—Henry R. Jiles
*Assistant Examiner*—Kurt G. Briscoe
*Attorney, Agent, or Firm*—Lawrence S. Levinson; Stephen B. Davis

[57] ABSTRACT

1,4-Dihydropyrimidines of the formula

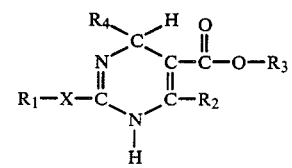

wherein X is sulfur or oxygen and $R_4$ is aryl or heterocyclo and disclosed. These compounds are useful as cardiovacular agents, particularly anti-hypertensive agents, due to their vasodilator activity.

23 Claims, No Drawings

2-SUBSTITUTED THIO OR OXY-4-ARYL OR HETEROCYCLO-5-CARBOXY-1,4-DIHYDROPYRIMIDINES, COMPOSITION CONTAINING THEM, AND METHOD OF USING THEM TO REDUCE BLOOD PRESSURE

RELATED APPLICATION

This application is a continuation-in-part of U.S. Ser. No. 736,151 filed on May 20, 1985 now abandoned.

BACKGROUND OF THE INVENTION

Stoltefuss et al. in German Offenlegungsschrift No. 3,234,684 A 1 disclose dihydropyrimidines of the formula

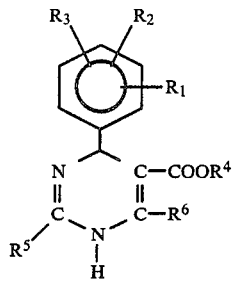

wherein $R^5$ is hydrogen, alkyl, substituted alkyl, phenyl, etc. These compounds are disclosed as possessing cardiovascular activity.

SUMMARY OF THE INVENTION

This invention is directed to the novel pyrimidine compounds of formula I and pharmaceutically acceptable salts thereof

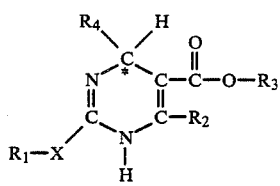 (I)

wherein:

X is oxygen or sulfur.

$R_1$ is lower alkyl, lower alkenyl, lower alkynyl, $-(CH_2)_m$—cycloalkyl, $-(CH_2)_m$—aryl, $-(CH_2)_n$—heterocyclo, $-(CH_2)_p$—OH, $-(CH_2)_p$—O—lower alkyl, $-(CH_2)_p$—O—$(CH_2)_m$—aryl, $-(CH_2)_p$—SH, $-(CH_2)_p$—S—lower alkyl, $-(CH_2)_p$—S—$(CH_2)_m$—aryl,

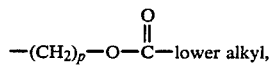

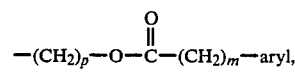

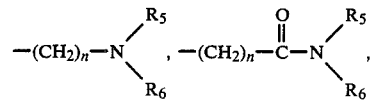

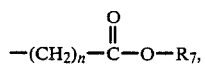

or halo substituted lower alkyl.

$R_2$ is hydrogen, lower alkyl, lower alkenyl, lower alkynyl, $-(CH_2)_m$—cycloalkyl, $-(CH_2)_m$—aryl, $-(CH_2)_n$—heterocyclo, $-(CH_2)_n$—OH, $-(CH_2)_n$—O—lower alkyl, $-(CH_2)_n$—O—$(CH_2)_m$—aryl, $-(CH_2)_n$—SH, $-(CH_2)_n$—S—lower alkyl, $-(CH_2)_n$—S—$(CH_2)_m$—aryl,

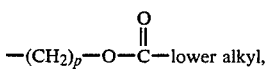

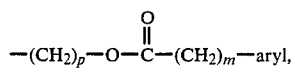

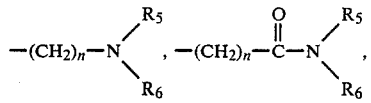

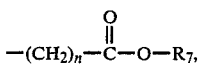

or halo substituted lower alkyl.

$R_3$ is hydrogen, lower alkyl, $-(CH_2)_m$—aryl, $-(CH_2)_m$—cycloalkyl, $-(CH_2)_n$—heterocyclo, $-(CH_2)_p$—OH, $-(CH_2)_p$—O—lower alkyl, $-(CH_2)_p$—O—$(CH_2)_m$—aryl, $-(CH_2)_p$—SH, $-(CH_2)_p$—S—lower alkyl, $-(CH_2)_p$—S—$(CH_2)_m$—aryl, $-(CH_2)_p$—O—$\overset{\overset{\displaystyle O}{\|}}{C}$—lower alkyl, $-(CH_2)_p$—O—$\overset{\overset{\displaystyle O}{\|}}{C}$—$(CH_2)_m$—aryl, $-(CH_2)_n$—N$\overset{R_5}{\underset{R_6}{\diagdown}}$ , $-(CH_2)_n$—$\overset{\overset{\displaystyle O}{\|}}{C}$—N$\overset{R_5}{\underset{R_6}{\diagdown}}$ , $-(CH_2)_n$—$\overset{\overset{\displaystyle O}{\|}}{C}$—O—$R_7$, halo substituted lower alkyl, or a pharmaceutically acceptable salt forming ion.

$R_4$ is aryl or heterocyclo.

$R_5$ and $R_6$ are independently selected from the group consisting of hydrogen, lower alkyl, and $-(CH_2)_m$—aryl or $R_5$ and $R_6$ together with the N atom to which they are attached complete a heterocyclic ring of the formula

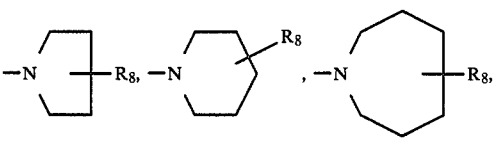

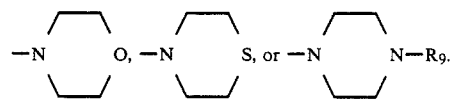

$R_7$ is hydrogen, lower alkyl, $-(CH_2)_m$—aryl, or a pharmaceutically acceptable salt forming ion.

$R_8$ is hydrogen, lower alkyl of 1 to 4 carbons, lower alkoxy of 1 to 4 carbons, lower alkylthio of 1 to 4 carbons, halo, hydroxy, or $CF_3$.

$R_9$ is hydrogen, lower alkyl of 1 to 4 carbons,

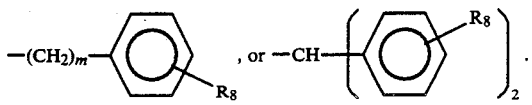

m is zero or an integer from 1 to 6.
n is an integer from 1 to 6.
p is an integer from 2 to 6.

DETAILED DESCRIPTION OF THE INVENTION

This invention in its broadest aspects relates to the pyrimidine compounds of formula I above, to compositions and the method of using such compounds as cardiovascular agents.

The term lower alkyl used in defining various symbols refers to straight or branched chain saturated hydrocarbon radicals having up to eight carbons, preferably from one to five carbons. Similarly, the terms lower alkoxy and lower alkylthio refer to such lower alkyl groups attached to an oxygen or sulfur.

The term lower alkenyl refers to straight or branched chain hydrocarbon radicals having from two to eight carbons and one double bond, preferably three to five carbons. The term lower alkynyl refers to straight or branched chain hydrocarbon radicals having from two to eight carbons and one triple bond, preferably three to five carbons.

The term cycloalkyl refers to saturated carbocyclic rings of 4 to 7 carbon atoms with cyclopentyl and cylohexyl being most preferred.

The term halo refers to chloro, bromo and fluoro.

The term halo substituted lower alkyl refers to such lower alkyl groups described above in which one or more hydrogens have been replaced by chloro, bromo or fluoro groups such as trifluoromethyl, which is preferred, pentafluoroethyl, 2,2,2-trichloroethyl, chlorometyl, bromomethyl, etc.

The term aryl refers to phenyl, 1-naphthyl, 2-napht-hyl, mono substituted phenyl, 1-naphthyl, or 2-naphthyl wherein said substituent is lower alkyl of 1 to 4 carbons, lower alkylthio of 1 to 4 carbons, lower alkoxy of 1 to 4 carbons, halo, nitro, cyano, hydroxy, amino, —NH—alkyl wherein alkyl is of 1 to 4 carbons, —N(alkyl)$_2$ wherein alkyl is of 1 to 4 carbons, $CF_3$, NCS, $OCHF_2$,

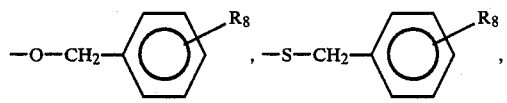

—O—CH$_2$—cycloalkyl, or —S—CH$_2$-cycloalkyl, and di-substituted phenyl, 1-naphthyl, or 2-naphthyl wherein said substituents are selected from methyl, methoxy, methylthio, halo, $CF_3$, nitro, amino, and $OCHF_2$.

The term heterocyclo refers to fully saturated or unsaturated rings of 5 or 6 atoms containing one to four N atoms, or one O atom, or one S atom, or one O atom and one or two N atoms, or one S atom and one or two N atoms. The heterocyclo ring is attached by way of an available carbon atom. Preferred monocyclic heterocyclo groups include 2- and 3-thienyl, 2- and 3-furyl, 2-, 3- and 4-pyridyl, and imidazolyl. The 2-, 3- and 4-pyridyl may also have a substituent selected from lower alkyl of 1 to 4 carbons, lower alkoxy of 1 to 4 carbons, and lower alkylthio of 1 to 4 carbons on an available carbon. The preferred substituted pyridyl is 2-methylthio-3-pyridinyl. The term heterocyclo also includes bicyclic rings wherein the five or six membered ring containing O, S and N atoms as defined above is fused to a benzene ring and the bicyclic ring is attached by way of an available carbon atom in the benzene ring. Preferred bicyclic heterocyclo groups include 4, 5, 6, or 7-indolyl, 4, 5, 6, or 7-isoindolyl, 5, 6, 7 or 8-quinolinyl, 5, 6, 7 or 8-isoquinolinyl, 4, 5, 6, or 7-benzothiazolyl, 4, 5, 6 or 7-benzoxazolyl, 4, 5, 6 or 7-benzimidazolyl, 4, 5, 6 or 7-benzoxadiazolyl, and 4, 5, 6 or 7-benzofurazanyl.

The compounds of formula I can be prepared as follows. For example, when X is sulfur or oxygen, the keto ester compound of the formula

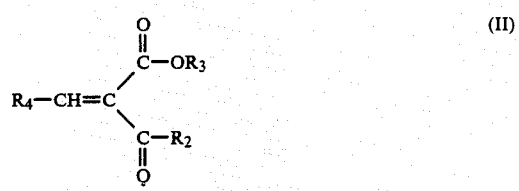

is reacted in a suitable solvent with the substituted urea-like compound of the formula

especially a salt thereof, in the presence of sodium acetate or sodium bicarbonate.

The substituted urea-like compound of formula III can be prepared by treating urea or thiourea with

wherein L is a leaving group such as Cl, Br, or I.

The compounds of formula I when X is sulfur can also be prepared by reacting a 2-thioxo-5-pyrimidinecarboxylic acid of the formula

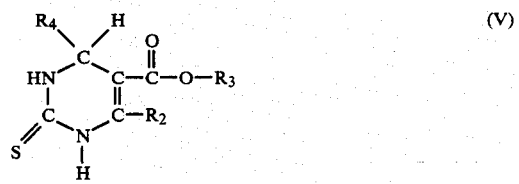

with the reactant of formula IV in the presence of potassium carbonate.

The 2-thioxo-5-pyrimidinecarboxylic acid starting material of formula V can be prepared by reacting an aldehyde of the formula

with the keto ester or acid of the formula

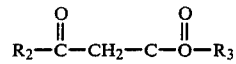 (VII)

and thiourea.

If any of $R_1$, $R_2$, $R_3$ and $R_4$ in the above reactions are aryl or —$(CH_2)_m$—aryl wherein aryl is phenyl substituted with one hydroxy or one or more amino groups, heterocyclo or —$(CH_2)_n$—heterocyclo wherein the heterocyclo ring contains an NH such as imidazolyl, or a substituted alkyl such as —$(CH_2)_n$—OH, —$(CH_2)_p$—OH, —$(CH_2)_p$—$NH_2$, —$(CH_2)_n$—SH, —$(CH_2)_p$—SH, or

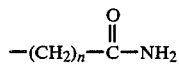

then the hydroxyl, amino, or mercaptan function should be protected during the reaction. Suitable protecting groups include benzyloxycarbonyl, t-butoxycarbonyl, benzyl, benzhydryl, etc. The protecting group is removed by hydrogenation, treatment with acid, or by other known means following completion of the reaction.

Preferred compounds of this invention are those wherein:

$R_1$ is lower alkyl of 1 to 5 carbons, especially methyl or pentyl, lower alkenyl of 3 to 5 carbons, especially 2-propenyl, benzyl, 4-methoxybenzyl, or

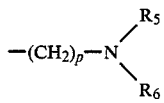

$R_2$ is lower alkyl of 1 to 5 carbons, especially methyl.

$R_3$ is lower alkyl of 1 to 5 carbons, —$(CH_2)_p$—O— lower alkyl wherein p is 2, 3 or 4 and lower alkyl is of 1 to 5 carbons,

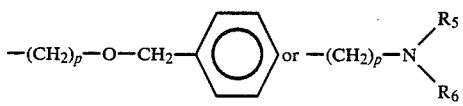

p is 2, 3 or 4.

$R_5$ and $R_6$ are independently selected from hydrogen, lower alkyl of 1 to 5 carbons, and benzyl.

$R_4$ is phenyl, mono substituted phenyl wherein said substituent is at the 2- or 3-position and is lower alkyl of 1 to 4 carbons, lower alkoxy of 1 to 4 carbons, lower alkylthio of 1 to 4 carbons, halo, $CF_3$, nitro, or $OCHF_2$, or di substituted phenyl at the 2- and 3-positions wherein said substituents are selected from methyl, methoxy, methylthio, halo, $CF_3$, nitro, or $OCHF_2$.

Most preferred are the above compounds wherein:
X is sulfur.
$R_1$ is 2-propenyl or

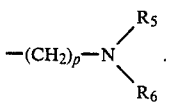

$R_2$ is methyl.

$R_3$ is ethyl, isopropyl, or

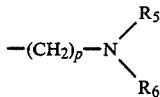

$R_5$ is methyl.
$R_6$ is methyl or benzyl.
p is 2 or 3.
$R_4$ is 2-nitrophenyl, 3-nitrophenyl, 2-(trifluoromethyl)phenyl, or 2,3-dichlorophenyl.

The compounds of formula I have been represented structurally as 1,4-dihydropyrimidines. However, such structures are tautomeric and can also be structurally represented as 3,4-dihydropyrimidines, i.e.,

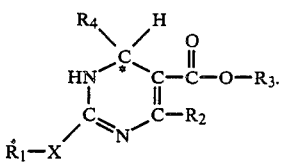

Both forms are within the scope of this invention.

The compounds of formula I contain an asymmetric center within the dihydropyrimidine ring as represented by the *. Thus, the compounds of formula I can exist in diastereomeric forms or in mixtures thereof. The above described processes can utilize racemates, enantiomers or diastereomers as starting materials. When diastereomeric products are prepared, they can be separated by conventional chromatographic or fractional crystallization methods.

The compounds of formula I form salts with a variety of inorganic and organic acids. The non-toxic pharmaceutically acceptable salts are preferred, although other salts may also be useful in isolating or purifying the product. Such pharmaceutically acceptable salts include those formed with hydrochloric acid, methanesulfonic acid, sulfuric acid, acetic acid, maleic acid, etc. The salts are obtained by reacting the product with an equivalent amount of the acid in a medium in which the salt precipitates.

In addition, the compounds of formula I in which $R_1$, $R_2$ or $R_3$ is

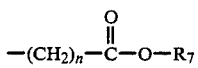

or in which $R_3$ is hydrogen include carboxylic acid salts, i.e., $R_3$ or $R_7$ is a pharmaceutically acceptable salt forming ion. Preferred salt forming ions include alkali metal salt ions such as sodium, potassium, and lithium, and alkaline earth metal salt ions such as calcium and magnesium.

The compounds of formula I and the pharmaceutically acceptable salts thereof are useful as cardiovascular agents. These compounds act as calcium entry blocking vasodilators and are especially useful as antihypertensive agents. Thus, by the administration of a composition containing one (or a combination) of the compounds of this invention the blood pressure of a hypertensive mammalian (e.g., human) host is reduced. A single dose, or preferably two to four divided daily doses, provided on a basis of about 0.1 to 100 mg. per kilogram of body weight per day, preferably from about 1 to about 50 mg. per kilogram per day, is appropriate to reduce blood pressure. The substance is preferably administered orally, but parenteral routes such as the subcutaneous, intramuscular, or intravenous routes can also be employed.

As a result of the calcium entry blocking activity of the compounds of formula I, it is believed that such compounds in addition to being anti-hypertensives may also be useful as antiarrhythmic agents, as anti-anginal agents, as antifibrillatory agents, as anti-asthmatic agents, and in limiting myocardial infarction.

The compounds of this invention can also be formulated in combination with a diuretic, or a beta-adrenergic agent, or angiotensin converting enzyme inhibitor. Suitable diuretics include the thiazide diuretics such as hydrochlorothiazide and bendroflumethiazide, suitable beta-adrenergic agents include nadolol, and suitable angiotensin converting enzyme inhibitors include captopril.

The compounds of formula I can be formulated for use in the reduction of blood pressure in compositions such as tablets, capsules or elixirs for oral administration, or in sterile solutions or suspensions for parenteral administration. About 10 to 500 mg. of a compound of formula I is compounded with physiologically acceptable vehicle, carrier, excipient, binder, preservative, stabilizer, flavor, etc., in a unit dosage form as called for by accepted pharmaceutical practice. The amount of active substance in these compositions or preparations is such that a suitable dosage in the range indicated is obtained.

The following examples are illustrative of the invention. Temperatures are given in degrees centigrade.

EXAMPLE 1

1,4-Dihydro-6-methyl-4-(3-nitrophenyl)-2-[(phenylmethyl)thio]-5-pyrimidinecarboxylic acid, ethyl ester (a)
1,2,3,4-Tetrahydro-6-methyl-4-(3-nitrophenyl)-2-thioxo-5-pyrimidinecarboxylic acid, ethyl ester A solution containing m-nitrobenzaldehyde (7.55 g., 50.0 mmole), ethylacetoacetate (6.5 g., 50.0 mmole), and thiourea (3.8 g., 50.0 mmole) in absolute ethanol (30 ml.) is treated with concentrated hydrochloric acid (0.2 ml.). The resulting reaction mixture is heated at reflux for 6 hours. It is then cooled to room temperature and triturated. A small amount of a white solid precipitates out. The reaction flask is then allowed to cool in the refrigerator overnight. The precipitate that forms is filtered off and washed with additional absolute ethanol to provide 2.5 g. of colorless solid product. Recrystallization from absolute ethanol gives an analytically pure sample of 1,2,3,4-tetrahydro-6-methyl-4-(3-nitrophenyl)-2-thioxo-5-pyrimidinecarboxylic acid, ethyl ester; m.p. 208°-209°. TLC (silica gel; ethyl acetate:hexane, 1:1) $R_f$=0.45.

Anal. calc'd. for $C_{14}H_{15}N_3O_4S$: C, 52.33; H, 4.71; N, 13.08; S, 9.98. Found: C, 52.28; H, 4.81; N, 13.10; S, 9.90.

(b)
1,4-Dihydro-6-methyl-4-(3-nitrophenyl)-2[(phenylmethyl)thio]-5-pyrimidinecarboxylic acid, ethyl ester A suspension of 1,2,3,4-tetrahydro-6-methyl-4-(3-nitrophenyl)-2-thioxo-5-pyrimidinecarboxylic acid, ethyl ester (400 mg., 1.24 mmole), potassium carbonate (270 mg., 2.0 mmole) and benzyl bromide (240 mg., 1.4 mmole) in acetone (7.0 ml.) is stirred at room temperature overnight. The solid is filtered off and the filtrate is diluted with ethyl acetate. The solution is washed with water and brine, and is dried over anhydrous magnesium sulfate. Evaporation of the solvent provides a light yellow solid which is triturated with isopropyl ether and filtered off to give 370 mg. of product. This material is combined with product from another run (150 mg.) and recrystallized from isopropyl etherdichloromethane to give 1,4-dihydro-6-methyl-4-(3-nitrophenyl)-2-[(phenylmethyl)thio]-5-pyrimidinecarboxylic acid, ethyl ester as light yellow crystals; m.p. 129°-130°. TLC (silica gel; ethyl acetate:hexane, 40:60) $R_f$=0.39.

Anal. calc'd. for $C_{21}H_{21}N_3O_4S$: C, 61.30; H, 5.14; N, 10.21; S, 7.79, Found: C, 61.30; H, 5.16; N, 9.96; S, 7.58.

EXAMPLE 2

1,4-Dihydro-6-methyl-2-(methylthio)-4-(3-nitrophenyl)-5-pyrimidinecarboxylic acid, ethyl ester A suspension of 1,2,3,4-tetrahydro-6-methyl-4-(3-nitrophenyl)-2-thioxo-5-pyrimidinecarboxylic acid, ethyl ester (1.0 g., 3.1 mmole) in dry acetone (10 ml.) is treated with finely ground potassium carbonate (1.0 g.) and methyl iodide (220 μl., 3.5 mmole). The reaction flask is tightly stoppered and the suspension is allowed to stir at room temperature overnight. It is then diluted with ethyl acetate and the white solid is filtered off. The filtrate is washed with water and brine. After drying over anhydrous magnesium sulfate, the solvent is stripped off to give a light yellow foam. Crystallization from etherhexane provides 820 mg. of off-white crystalline product. This material is combined with that from another run (200 mg.) and triturated with hexane to give an analytically pure sample of 1,4-dihydro-6-methyl-2-(methylthio)-4-(3-nitrophenyl)-5-pyrimidinecarboxylic acid, ethyl ester; m.p. 91.5°-93°. TLC (silica gel; ethyl acetate: hexane, 40:60) $R_f$=0.36.

Anal. calc'd. for $C_{15}H_{17}N_3O_4S$: C, 53.72; H, 5.11; N, 12.53; S, 9.56 Found: C, 53.80; H, 5.19; N, 12.38; S, 9.37.

EXAMPLE 3

1,4-Dihydro-6-methyl-4-(3-nitrophenyl)-2-(2-propenylthio)-5-pyrimidinecarboxylic acid, ethyl ester A suspension of 1,2,3,4-tetrahydro-6- methyl-4-(3-nitrophenyl)-2-thioxo-5-pyrimidinecarboxylic acid, ethyl ester (1.3 g., 4.05 mmole), finely ground potassium carbonate (1.3 g.) and allyl bromide (539 mg., 4.45 mmole) in acetone is stirred at room temperature overnight. The reaction is diluted with ethyl acetate and filtered through a celite pad. The filtrate is washed with water and brine. After drying over anhydrous magnesium sulfate, the solvent is stripped off. The residue is purified by flash chromatography (5% ethyl acetate in methylene chloride) to provide 1.29 g. of a colorless oil. Crystallization from isopropyl ether-hexane yields 1.11 g. of 1,4-dihydro-6-methyl-4-(3-nitrophenyl)-2-(2-propenylthio)-5-pyrimidinecarboxylic acid, ethyl ester; m.p. 91°-93°. TLC (silica gel; ethyl acetate:hexane, 40:60) $R_f$=0.40.

Anal. calc'd. for $C_{17}H_{19}N_3O_4S$: C, 56.50; H, 5.30; N, 11.63; S, 8.87. Found: C, 56.49; H, 5.24; N, 11.40; S, 8.78.

EXAMPLE 4

1,4-Dihydro-6-methyl-4-(3-nitrophenyl)-2-(pentylthio)-5-pyrimidinecarboxylic acid, ethyl ester A suspension of 1,2,3,4-tetrahydro-6-methyl-4-(3-nitrophenyl)-2-thioxo-5-pyrimidinecarboxylic acid, ethyl ester (1.3 g., 4.05 mmole) in acetone (10 ml.) and N,N-dimethylformamide (7 ml.) is treated with finely ground potassium carbonate (1.3 g.) and 1-bromopentane (672 mg.,m 0.55 ml., 4.45 mmole). The reaction is allowed to stir at room temperture for 48 hours. The yellow suspension is diluted with ethyl acetate and is filtered through a celite pad. The filtrate is washed with water, washed with brine, and dried over anhydrous magnesium sulfate. Evaporation provides a yellow solid that is purified by flash chromatography (5% ethyl acetate in dichloromethane). The resulting product is crystallized from isopropyl ether-hexane to give 1.18 g. of 1,4-dihydro-6-methyl-4-(3-nitrophenyl)-2-(pentylthio)-5-pyrimidinecarboxylic acid, ethyl ester as colorless crystals; m.p. 103.5°–105°. TLC (silica gel; ethyl acetate:hexanes, 40:60) $R_f=0.48$.

Anal. calc'd. for $C_{19}H_{25}N_3O_4S$:

C, 58.29; H, 6.44; N, 10.73; S, 8.19. Found: C, 58.26; H, 6.42; N, 10.60; S, 8.19.

EXAMPLES 5–29

Following the procedure of Examples 1 to 4, the aldehyde shown in Col. 1 is treated with the keto ester shown in Col. II and thiourea to give the intermediate shown in Col. III. Treatment with the reagent shown in Col. IV wherein L is a leaving group such as Cl, Br, or I yields the final product shown in Col. V.

|  | Col. I | Col. II | | Col. III | | Col. IV | | Col. V |
|---|---|---|---|---|---|---|---|---|
|  | $R_4$—CHO | $R_2$—C(O)—CH$_2$—C(O)—O—$R_3$ | | (structure with HN, R$_4$, C=S, $R_2$, $R_3$) | | $R_1$—L | | (structure with $R_1$—S, N, $R_2$, $R_3$, $R_4$) |
| Example | $R_1$ | | $R_2$ | | $R_3$ | | $R_4$ | |
| 5 | —CH$_2$—(cyclohexyl) | | —CH$_3$ | | —CH$_2$CH$_3$ | | —(phenyl) | |
| 6 | —CH$_2$—CH=CH$_2$ | | —CH$_3$ | | —CH$_2$—(phenyl) | | —(naphthyl-NO$_2$) | |
| 7 | —CH$_2$—CH$_2$—CH=CH$_2$ | | —C$_2$H$_5$ | | —CH$_2$—(thienyl) | | —(naphthyl-NO$_2$) | |
| 8 | —CH$_2$—(phenyl) | | —CH$_3$ | | —CH$_2$—CH$_2$—O—CH$_3$ | | —(phenyl-CF$_3$) | |
| 9 | —(CH$_2$)$_3$—CH$_2$Cl | | —CH$_3$ | | —CH$_2$—CH$_2$—S—C$_2$H$_5$ | | —(phenyl-Cl,Cl) | |
| 10 | —CH$_2$—(thienyl) | | —CH$_3$ | | —CH$_2$—CH$_2$—O—CH$_2$—(phenyl) | | —(phenyl-CH$_3$) | |

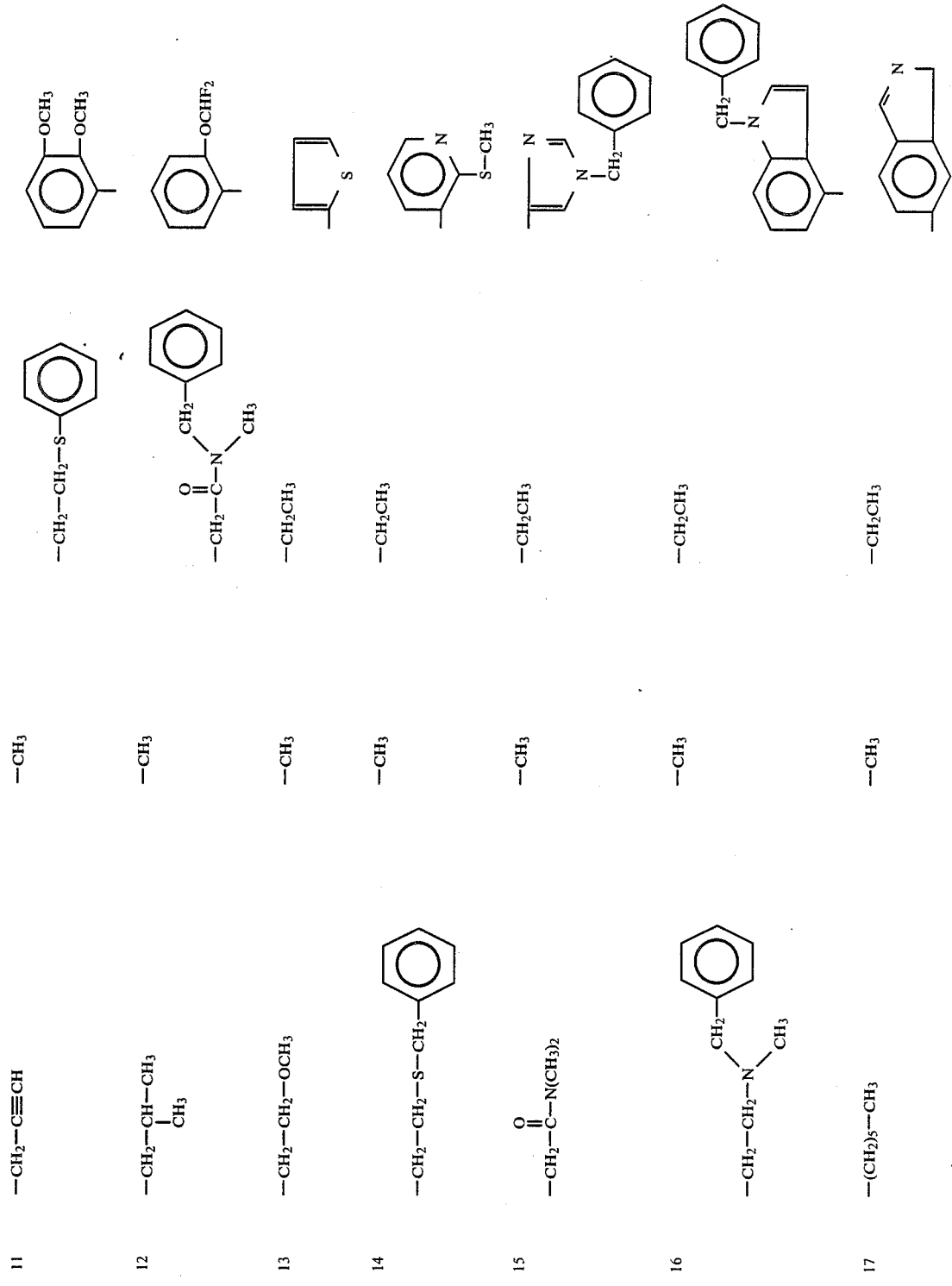

-continued

| | | | |
|---|---|---|---|
| 18 | —CH₂CH=CH₂ | —CH₃ | —CH₂CH₃ |
| 19 | —CH₂CH=CH₂ | —CH₃ | —CH₂CH₃ |
| 20 | —(CH₂)₂—N(morpholino) | —CH₃ | —CH₂CH₃ |
| 21 | —CH₂CH=CH₂ | —CH₃ | —CH₂CH₃ |
| 22 | —(CH₂)₂—N(piperazinyl-N-CH₂-phenyl) | —CH₃ | —CH₂CH₃ |
| 23 | —CH₂—(4-Cl-phenyl) | —CH₃ | —CH₂CH₃ |
| 24 | —CH₂CH=CH₂ | —CH₃ | —CH₂CH₃ |
| 25 | —CH₂CH=CH₂ | —CH₂—phenyl | —CH₂CH₃ |

-continued

| | | | |
|---|---|---|---|
| 26 | —CH₂CH=CH₂ | —CF₃ | —CH₂CH₃ |
| 27 | —CH₂CH=CH₂ | —CH₂—O—CH₃ | —CH₂CH₃ |
| 28 | —CH₂CH=CH₂ | —CH₂—S—C₂H₅ | —CH₂CH₃ |
| 29 | —CH₂CH=CH₂ | —CH₂—⌬ (phenyl) | —CH₂CH₃ |
| 30 | —(CH₂)₂—N[piperidine with N—CH(phenyl)₂] | —CH₃ | —CH(CH₃)₂ |

Substituents on phenyl ring (col. 4): 
- 26: 2-SCH₃
- 27: 2-CF₃
- 28: 2,3-Cl₂
- 29: 2-NO₂
- 30: 2,3-Cl₂

The N—protecting groups in Examples 15 and 16 are removed as the last step in the synthesis.

EXAMPLE 31

4-(2,3-Dichlorophenyl)-1,4-dihydro-6-methyl-2-(methylthio)-5-pyrimidinecarboxylic acid, ethyl ester, monohydrochloride A suspension containing 2-[(2,3-dichlorophenyl)methylene-3-oxobutanoic acid, ethyl ester (3.0 g., 10.45 mmole), S-methylthiopseudourea sulfate (2.9 g., 10.43 mmole) and sodium acetate (1.8 g., 21.9 mmole) in isopropanol (12 ml.) is heated overnight. The reaction (yellow suspension) is diluted with dichloromethane and filtered. The filtrate is evaporated and the resulting residue is taken up in ethyl acetate. The solution is washed with water, sodium bicarbonate, and brine. After drying over anhydrous magnesium sulfate, the solvent is stripped off to provide a yellow foam. This material is purified by flash chromatography (5% ethyl acetate in dichloromethane) to give a colorless foam (2.3 g.). This material is dissolved in dichloromethane and then treated with excess methanolic hydrochloric acid (4 ml. of 4N solution). The solvent is stripped off and the residue is crystallized from isopropanol-methylene chloride to yield 2.38 g. of 4-(2,3-dichlorophenyl)-1,4-dihydro-6-methyl-2-(methylthio)-5-pyrimidinecarboxylic acid, ethyl ester, monohydrochloride as a colorless crystalline material; m.p. 199.5°-201.5° (with evolution of gas). TLC(silica gel; ethyl acetate:dichloromethane, 10:90) $R_f$=0.42.

Anal. calc'd. for $C_{15}H_{16}Cl_2N_2O_2S \cdot HCl$: C, 45.53; H, 4.33; N, 7.08; S, 8.10; Cl, 26.88. Found: C, 45.62; H, 4.41; N, 6.82; S, 8.12; Cl, 26.85.

EXAMPLE 32

1,4-Dihydro-6-methyl-2-(methylthio)-4-(2-nitrophenyl)-5-pyrimidinecarboxylic acid, ethyl ester, monohydrochloride A reaction mixture containing 2-[(2-nitrophenyl)methylene]-3-oxobutanoic acid, ethyl ester (2.63 g., 10.0 mmole), S-methylthiopseudourea sulfate (2.78 g., 10.0 mmole) and sodium acetate (1.8 g., 21.9 mmole) is allowed to stir at room temperature for about 72 hours. The reaction is diluted with methylene chloride and filtered. The filtrate is evaporated to provide a yellow semisolid. This material is taken up in ethyl acetate and washed with water, sodium bicarbonate, and brine. After drying over anhydrous magnesium sulfate, the solvent is evaporated to provide a yellow foam which is crystallized from isopropyl ether-hexanes to give 2.55 g. of a yellow solid containing impurities. This material is dissolved in methylene chloride and treated with methanolic hydrochloric acid (2 ml. of 4N solution). The solvent is stripped and the residue is crystallized from isopropanol-methylene chloride to provide 2.06 g. of 1,4-dihydro-6-methyl-2-(methylthio)-4-(2-nitrophenyl)-5-pyrimidinecarboxylic acid, ethyl ester, monohydrochloride as colorless crystals (yellow tinge); m.p. 188.5°-190.5° (with gas evolution). TLC (silica gel; ethyl acetate:dichloromethane, 10:90) $R_f$=0.42.

Anal. calc'd. for $C_{15}H_{17}N_3O_4S \cdot HCl$: C, 48.45; H, 4.88; N, 11.30; S, 8.62; Cl, 9.52. Found: C, 48.50; H, 4.93; N, 11.39; S, 8.52; Cl, 9.51.

EXAMPLE 33

1,4-Dihydro-6-methyl-2-(methylthio)-4-[2-(trifluoromethyl)phenyl]-5-pyrimidinecarboxylic acid, ethyl ester, monohydrochloride A reaction mixture containing 2-[[2-(trifluoromethyl)phenyl]methylene]-3-oxobutanoic acid, ethyl ester (3.2 g., 11.18 mmole), S-methylthiopseudourea sulfate (2.78 g., 10 mmole), and sodium acetate (1.8 g., 21.9 mmole) in isopropanol (12 ml.) is allowed to stir at room temperature for 48 hours. The reaction mixture is then diluted with dichloromethane and filtered. The filtrate is evaporated and the residue is dissolved in ethyl acetate. The solution is washed with water, sodium bicarbonate and brine. After drying over anhydrous magnesium sulfate, the solvent is stripped off to give a yellow oil. Purification by flash chromatography (5% ethyl acetate in dichloromethane) yields a colorless oil. This oil is taken up in dichloromethane, treated with methanolic hydrochloric acid (3 ml. of 4N solution) and the solvent is then stripped off. The residue is recrystallized from isopropanol to give 1.89 g. of 1,4-dihydro-6-methyl-2-(methylthio)-4-[2-(trifluoromethyl)phenyl]-5-pyrimidinecarboxylic acid, ethyl ester, monohydrochloride as a colorless solid; m.p. 175.5°-177° (with evolution of gas). TLC (silica gel; ethyl acetate:dichloromethane,10:90) $R_f$=0.38.

Anal. calc'd. for $C_{16}H_{17}F_3N_2O_2S \cdot HCl$: C, 48.67; H, 4.60; N, 7.09; S, 8.12; Cl, 8.98; F, 14.44. Found: C, 48.76; H, 4.61; N, 7.16; S, 7.94; Cl, 9.07; F, 14.50.

EXAMPLE 34

1,4-Dihydro-2-methoxy-6-methyl-4-(3-nitrophenyl)-5-pyrimidinecarboxylic acid, ethyl ester A reaction mixture containing 2-[(3-nitrophenyl)methylene]-3-oxobutanoic acid, ethyl ester (2.62 g., 10.0 mmole), 2-methylpseudourea sulfate (1.72 g., 10.0 mmole), and sodium acetate (1.8 g., 22.0 mmole) in tetrahydrofuran (10 ml.) is heated under reflux for 4 hours. The reaction mixture is allowed to cool to room temperature, diluted with ethyl acetate, and filtered. The filtrate is washed with sodium bicarbonate and brine, and then dried over anhydrous magnesium sulfate. Evaportion of the solvent gives a yellow oil which is purified by flash chromatography (5% ethyl acetate in dichloromethane). The resulting foam is crystallized from isopropanolhexanes to provide 1.53 g. of 1,4-dihydro-2-methoxy-6-methyl-4-(3-nitrophenyl)-5-pyrimidinecarboxylic acid, ethyl ester as a colorless crystalline product; m.p. 103.5°-105°. TLC (silica gel; ethyl acetate:hexanes, 50:50) $R_f$=0.31.

Anal. calc'd. for $C_{15}H_{17}N_3O_5$: C, 56.42; H, 5.37; N, 13.16. Found: C, 56.52; H, 5.35; N, 13.03.

EXAMPLE 35

1,4-Dihydro-6-methyl-2-(methylthio)-4-[2-(trifluoromethyl)phenyl]-5-pyrimidinecarboxylic acid, 2-[methyl(phenylmethyl)amino]ethyl ester, oxalate salt (1:1.5)

A solution of 2-[[2-(trifluoromethyl)phenyl]methylene]-3-oxobutanoic acid, 2-[methyl(phenylmethyl)amino]ethyl ester (2.4 g., 6.0 mmole) in isopropanol (10 ml.) is treated with S-methylthiopseudourea sulfate (1.14 g., 40 mmole) and sodium acetate (656 mg., 8.0 mmole). The reaction is allowed to stir at room temperature for 72 hours. It is then diluted with ethyl acetate and washed with water, sodium bicarbonate, and brine. After drying over anhydrous magnesium sulfate, the solvent is stripped to provide a yellow foam. This material is purified by flash chromatography (30% ethyl acetate in hexanes) to yield 1.55 g. of a yellow oil. This oil is dissolved in isopropanol (10 ml.) and is treated with a solution of oxalic acid (2.92 mg., 3.25 mmole) in isopropanol. A white precipitate that forms slowly goes in solution. Most of the isopropanol is evaporated and the residue is triturated with isopropyl ether to give 1.51 g. of a yellow, homogeneous, solid. This product is taken up in isopropanol (5 ml.) and isopropyl ether is slowly added until the solution becomes cloudy. Trituration gives 1.1 g. of 1,4-dihydro-6-methyl-2-(methylthio)-4-[2-(trifluoromethyl)phenyl]-5-pyrimidinecarboxylic acid, 2-[methyl(phenylmethyl)amino]ethyl ester, oxalate salt (1:1.5) as a light yellow solid; m.p. 116°–120° with effervescence (sinters at about 82°). TLC (silica gel; acetone:hexanes, 50:50) $R_f$=0.5.

Anal. calc'd. for $C_{27}H_{29}O_8N_3SF_3.0.1$ isopropyl ether: C, 53.22; H, 4.92; N, 6.74; S, 5.14; F, 9.15. Found: C, 53.26; H, 4.88; N, 6.57; S, 5.00; F, 9.19.

EXAMPLE 36

1,4-Dihydro-2-[[(4-Methoxyphenyl)methyl]thio]-6-methyl-4-(3-nitrophenyl)-5-pyrimidinecarboxylic acid, methyl ester A solution of 2-[(3-nitrophenyl)methylene]-3-oxobutanoic acid, methyl ester (5.0 g., 0.02 mole) in dimethylformamide (20 ml.) under argon at room temperature is treated with S-(4-methoxybenzyl)thiopseudourea hydrochloride (4.65 g., 0.02 mole, prepared from equivalent amounts of 4-methoxybenzyl chloride and thiourea in tetrahydrofuran) in one portion. The mixture is then heated at 65° for 3 hours. Upon cooling, the mixture is diluted with ethyl acetate and washed with water (twice), aqueous sodium bicarbonate, and saturated brine. The aqueous fractions are back-extracted with fresh ethyl acetate. The combined organic fractions are dried (magnesium sulfate) and concentrated in vacuo to give 9.0 g. of crude product. Crystallization from acetone/isopropyl ether gives 6.8 g. of 1,4-dihydro-2-[[(4-methoxyphenyl)methyl]thio]-6-methyl-4-(3-nitrophenyl)-5-pyrimidinecarboxylic acid, methyl ester; m.p. 125°–127.5°. TLC (silica gel; ethyl acetate:hexanes, 1:1) $R_f$=0.48.

Anal. calc'd. for $C_{21}H_{21}N_3O_5S$: C, 59.00; H, 4.95; N, 9.83; S, 7.50. Found: C, 58.86; H, 4.82; N, 9.51; S, 7.25.

EXAMPLE 37

4-(2,3-Dichlorophenyl)-1,4-dihydro-2-[[(4-methoxyphenyl)methyl]thio]-6-methyl-5-pyrimidinecarboxylic acid, 1-methylethyl ester, monohydrochloride A mixture of 2-[(2,3-dichlorophenyl)methylene]-3-oxobutanoic acid, 1-methylethyl ester (15.0 g., 0.049 mole), S-(4-methoxybenzyl)thiopseudourea hydrochloride (11.5 g., 0.049 mole), and sodium acetate (4.0 g., 0.049 mole) in dimethylformamide (90 ml.) is stirred and heated at 70° for 4 hours. After cooling, ether is added followed by extraction with water, sodium bicarbonate, and brine. The dried solution is evaporated to give 24.8 g. of an impure oily product. This material is flash chromatographed using ethyl acetate:haxane (1:3) to give 16.5 g. of an oil. A solution of this material in isopropyl ether yields 12.8 g. of colorless 4-(2,3-dichlorophenyl)-1,4-dihydro-2-[[(4-methoxyphenyl)methyl]thio]-6-methyl-5-pyrimidinecarboxylic acid, 1-methylethyl ester; m.p. 98°–100°.

Anal. calc'd. for $C_{23}H_{24}N_2Cl_2O_3S$: C, 57.61; H, 5.04; N, 5.84; S, 6.68. Found: C, 57.66; H, 5.02; N, 5.75; S, 6.64.

A solution of the above product (0.75 g.) in chloroform is treated with one equivalent of ethereal hydrochloric acid. The solution is evaporated and the oil residue is treated with ether to form 0.7 g. of colorless 4-(2,3-dichlorophenyl)-1,4-dihydro-2-[[(4-methoxyphenyl)methyl]thio]-6-methyl-5-pyrimidinecarboxylic acid, 1-methylethyl ester, monohydrochloride; m.p. 96°–98° (dec.). TLC (silica gel; ethyl aceate:hexane, 1:2) $R_f$=0.40.

Anal. calc'd. for $C_{23}H_{24}N_2Cl_2O_3S$ HCl C,53.54; H,4.88; N,5.43; Cl, 20.61; S,6.21. Found: C,53.61; H,4.97; N,5.47; Cl, 20.59; S,6.42.

EXAMPLE 38

1,4-Dihydro-2-[[(4-methoxyphenyl)methyl]thio]-6-methyl-4-(3-methylphenyl)-5-pyrimidinecarboxylic acid, ethyl ester A mixture of S-(4-methoxybenzyl)thiopseudourea hydrochloride (2.5 g., 10.7 mmole), 2-[(3-methylphenyl)methylene]-3-oxobutanoic acid, ethyl ester (2.5 g., 10.7 mmole) and sodium acetate (0.84 g., 10.7 mmole) in dimethylformamide (12 ml.) is stirred and heated at 70° for 6 hours. After cooling, ether is added followed by water, sodium bicarbonate, and brine. The dried solution is evaporated to give 4.4 g. of an impure oily product. Flash chromatography using ethyl acetate:hexane (1:4) gives 2.5 g. of 1,4-dihydro-2-[[(4-methoxyphenyl)methyl]thio]-6-methyl-4(3-methylphenyl)-5-pyrimidinecarboxylic acid, ethyl ester as an oil which slowly solidifies; m.p. 65°–67°.

Anal. calc'd. for $C_{23}H_{26}N_2O_3S$: C, 67.28; H, 6.38; N, 6.82. Found: C, 67.44; H, 6.52; N, 6.72.

EXAMPLES 39–59

Following the procedure of Examples 31 to 38, the keto ester shown in Col. I is reacted with the pseudourea shown in Col. II to give the final product shown in Col. III.

| | | Col. I | Col. II | Col. III | |
|---|---|---|---|---|---|
| | | $R_4-CH=C(C(=O)R_2)-C(=O)-O-R_3$ | $R_1-X-C(=NH)-NH_2$ | pyrimidine product | |
| Example | X | $R_1$ | $R_2$ | $R_3$ | $R_4$ |
| 39 | S | —CH₂—CH=CH₂ | —CH₃ | —CH₂CH₃ | 2-NO₂-phenyl 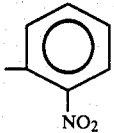 |
| 40 | S | —CH₂—CH=CH₂ | —CH₃ | —CH₂CH₃ | 3-CF₃-phenyl 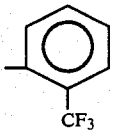 |
| 41 | S | —CH₂—CH=CH₂ | —CH₃ | —CH₂CH₃ | 2,3-Cl₂-phenyl 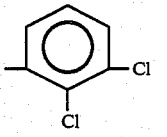 |
| 42 | S | —CH₂—CH=CH₂ | —CH₃ | —CH₂CH₃ | 2-OCHF₂-phenyl 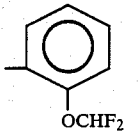 |
| 43 | O | —CH₂—CH=CH₂ | —CH₃ | —CH₂CH₃ | 2-CN-phenyl 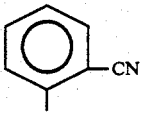 |
| 44 | S | —CH₂—CH=CH₂ | —CH₃ | —CH₂CH₃ | 7,8-Cl₂-naphthyl 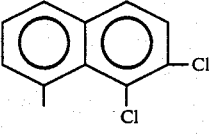 |
| 45 | O | —CH₂—CH₂—CH=CH₂ | —CH₃ | —CH₂CH₃ | 4-Br-phenyl 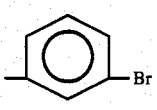 |
| 46 | S | —CH₂-phenyl 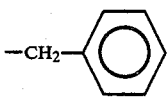 | —CF₃ | —CH₂CH₃ | furyl 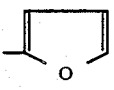 |
| 47 | O | —(CH₂)₂-phenyl 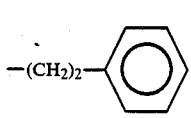 | -phenyl 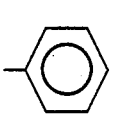 | —CH₂-phenyl 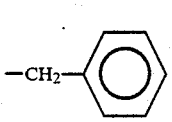 | 2-(SCH₃)-pyridyl 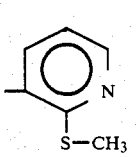 |

-continued

| | | Col. I | Col. II | Col. III | |
|---|---|---|---|---|---|
| | | R₄—CH=C(COOR₃)(C(=O)R₂) | R₁—X—C(=NH)NH₂ | dihydropyrimidine | |

| Example | X | R₁ | R₂ | R₃ | R₄ |
|---|---|---|---|---|---|
| 48 | S | —CH₂—cyclohexyl | —CH₂—O—CH₃ | —CH₂CH₃ | 3-pyridyl |
| 49 | O | —(CH₂)₂—O—C₂H₅ | —CH₃ | —CH₂CH₃ | 1-benzylimidazol-4-yl |
| 50 | S | —(CH₂)₂—S—phenyl | —H | —CH₂CH₃ | 1-benzylindol-4-yl |
| 51 | S | —(CH₂)₄—CH₃ | —CH₃ | —CH₂CH₂—N(CH₃)₂ | isoindol-4-yl |
| 52 | O | —(CH₂)₄—CH₃ | —CH₃ | —CH₂—C(=O)—OC₂H₅ | quinolin-5-yl |
| 53 | S | —CH₂CH₂CH=CH₂ | —CH₃ | —CH₂—CH₂—N(piperazinyl-N'—CH₃) | benzothiazol-4-yl |
| 54 | S | —CH₂CH=CH₂ | —CH₃ | —CH₂CH₂N(CH₃)(CH₂-phenyl) | benzoxazol-4-yl |
| 55 | S | —CH₂CH=CH₂ | —CH₃ | —(CH₂)₂—O—C₂H₅ | 1-benzylbenzimidazol-4-yl |

-continued

| | | Col. I | Col. II | Col. III | |
|---|---|---|---|---|---|
| Example | X | $R_1$ | $R_2$ | $R_3$ | $R_4$ |
| 56 | O | —$CH_3$ | —$CH_3$ | —$CH_2CH_3$ | 2-(1,2,3-benzoxadiazol)yl |
| 57 | S | —$(CH_2)_2$—$CH_3$ | —$CH_3$ | —$(CH_2)_2$—S—$CH_3$ | 2-(1,2,3-benzoxadiazol)yl |
| 58 | S | —$CH_2$—CH=$CH_2$ | —$CH_3$ | —$CH_2CH_2N(CH_3)_2$ | 2,3-dichlorophenyl |
| 59 | S | —$CH_2$—CH=$CH_2$ | —$CH_3$ | —$CH_2CH_3$ | 2-chloro-3-nitrophenyl |

The N protecting groups shown in Examples 49, 50 and 55 are removed as the last step in the synthesis.

EXAMPLE 60

4-(2,3-Dichlorophenyl)-1,4-dihydro-6-methyl-2(2-propenylthio)-5-pyrimidinecarboxylic acid, 1-methylethyl ester, monohydrochloride (a)
4-(2,3-Dichlorophenyl)-1,2,3,4-tetrahydro-6-methyl-2-thioxo-5-pyrimidinecarboxylic acid, 1-methylethyl ester A solution of 4-(2,3-dichlorophenyl)-1,4-dihydro-2-[[(4-methoxyphenyl)methyl]thio]-6-methyl-5-pyrimidinecarboxylic, 1-methylethyl ester (5.0 g., 10 mmole), trifluoroacetic acid (3.86 ml., 42 mmole), and ethyl mercaptan (1.56 g., 23 mmole) in dichloromethane (60 ml.) is stirred for 16 hours at room temperature and then refluxed for 4 hours to complete the reaction. The solvent is evaporated to give a colorless solid. Trituration with isopropyl ether yields 3.0 g. of 4-(2,3-dichlorophenyl)-1,2,3,4-tetrahydro-6-methyl-2-thioxo-5-pyrimidinecarboxylic acid, 1-methylethyl ester; m.p. 258°–260°.

Anal. calc'd. for $C_{15}H_{16}N_2Cl_2O_2S$: C, 50.14; H, 4.48; N, 7.79. Found: C, 49.89; H, 4.41; N, 7.59.

(b)
4-(2,3-Dichlorophenyl)-1,4-dihydro-6-methyl-2-(2-propenylthio)-5-pyrimidinecarboxylic acid, 1-methylethyl ester, monohydrochloride A solution of 4-(2,3-dichlorophenyl)-1,2,3,4-tetrahydro-6-methyl-2-thioxo-5-pyrimidinecarboxylic acid, 1-methylethyl ester (1.3 g., 3.6 mmole), allyl bromide (0.52 g., 4.3 mmole), 4-dimethylaminopyridine (0.44 g., 3.6 mmole), and sodium iodide (0.02 g.) in tetrahydrofuran (50 ml.) is refluxed for 16 hours. To complete the reaction, additional allyl bromide (0.26 g., 2.2 mmole) is added and heating is continued for 10 hours. The mixture is cooled, filtered, and washed with water to give 0.95 g. of colorless product as the hydrogen bromide salt; m.p. 253°–255°. This material is converted to 0.75 g. of base (sodium bicarbonate, ethyl acetate). An ether solution of this base material is treated with one equivalent of ethereal hydrochloric acid to give 0.81 g. of colorless 4-(2,3-dichlorophenyl)1,4-dihydro-6-methyl-2-(2-propenylthio)-5-pyrimidinecarboxylic acid, 1-methylethyl ester, monohydrochloride; m.p. 253°–255°. TLC (silica gel; ethyl acetate:hexane, 1:2) $R_f$=0.55.

Anal. calc'd. for $C_{18}H_{20}N_2Cl_2O_2S\cdot HCl$: C, 49.60; H, 4.85; N, 6.42; Cl, 24.20; S, 7.35. Found: C, 49.75; H, 4.92; N, 6.43; Cl, 24.40; S, 7.69.

EXAMPLE 61

4-(2,3-Dichlorophenyl)-1,4-dihydro-6-methyl-2-[[3-[methyl(phenylmethyl)amino]propyl]thio]-5-pyrimidinecarboxylic acid, 1-methylethyl ester, dihydrochloride A mixture of 4-(2,3-dichlorophenyl)-1,2,3,4-tetrahydro-6-methyl-2-thioxo-5-pyrimidinecarboxylic acid, 1-methylethyl ester (1.0 g., 2.7 mmole), [3-[methyl(phenylmethyl)amino]propyl]chloride (0.76 g., 3.8 mmole) and potassium carbonate (0.76 g., 5.4 mmole) in dimethylformamide (12 ml.) is stirred and heated at 70° for 4 hours, cooled, and then diluted with ethyl acetate. Extraction with water (twice) and brine, drying, and evaporating off the solvent gives 1.9 g. of an oil. Flash chromatography using ethyl acetate:hexane (2:1) gives 1.1 g. of 4-(2,3-dichlorophenyl)-1,4-dihydro-6-methyl-2-[[3-[methyl(phenylmethyl)amino]propyl]thio]-5-pyrimidinecarboxylic acid, 1-methylethyl ester as an oil.

Anal. calc'd. for $C_{26}H_{31}N_3Cl_2O_2S$: C, 59.99; H, 6.00; N, 8.07. Found: C, 60.00; H, 6.29; N, 7.81.

The above oil is dissolved in ethyl acetate and treated with two equivalents of ethanolic hydrochloric acid. The solvent is evaporated and the oil gradually solidifies. Trituration with ether gives 0.98 g. of 4-(2,3-dichlorophenyl)-1,4-dihydro-6-methyl-2-[[3-[methyl(phenylmethyl)amino]propyl]thio]-5-pyrimidinecarboxylic acid, 1-methylethyl ester, dihydrochloride as a colorless solid; m.p. 136°-139°. TLC (base) (silica gel; ethyl acetate) $R_f=0.25$.

Anal. calc'd. for $C_{26}H_{31}N_3Cl_2O_2S.2HCl$ C, 52.62; H, 5.60; N, 7.08; Cl, 23.89; S, 5.40. Found: C, 52.42; H, 5.69; N, 7.01; Cl, 23.76; S, 5.21.

EXAMPLE 62

4-(2,3-Dichlorophenyl)-2-[[2-(dimethylamino)ethyl]thio]-1,4-dihydro-6-methyl-5-pyrimidinecarboxylic acid, 1-methylethyl ester, dihydrochloride A mixture of 4-(2,3-dichlorophenyl)-1,2,3,4-tetrahydro-6-methyl-2-thioxo-5-pyrimidinecarboxylic acid, 1-methylethyl ester (1.85 g., 5.0 mmole), 2-dimethylaminoethyl chloride (2.15N toluene solution), and potassium carbonate (1.4 g., 10.0 mmole) in dimethylformamide (15 ml.) is stirred and heated for 3 hours at 70°, cooled, and diluted with ethyl acetate. The solution is washed with water (twice) and brine, dried, and evaporated to give 2.4 g. of an oil. This material is combined with 0.6 g. from another run. The combined oils are flash chromatographed using ethyl acetate:methanol (5:1) to give 1.53 g. of 4-(2,3-dichlorophenyl)-2-[[2-(dimethylamino)ethyl]thio]-1,4-dihydro-6-methyl-5-pyrimidinecarboxylic acid, 1-methylethyl ester as an oil.

Anal. calc'd. for $C_{19}H_{25}N_3Cl_2O_2S$: C, 53.02; H, 5.85; N, 9.76. Found: C, 52.48; H, 5.72; N, 9.62.

The above oil is dissolved in a solution of ether (20 ml.) and ethanol (2 ml.), then treated with 2 equivalents of ethanolic hydrochloric acid to give 1.55 g. of colorless solid 4-(2,3-dichlorophenyl)-2-[[2-(dimethylamino)ethyl]thio]-1,4-dihydro-6-methyl-5-pyrimidinecarboxylic acid, 1-methylethyl ester, dihydrochloride; m.p. 205°-207°. TLC (silica gel; ethyl acetate:methanol, 5:2) $R_f=0.25$.

Anal. calc'd. for $C_{19}H_{25}N_3Cl_2O_2S.2HCl$ C, 44.93; H, 5.40; N, 8.27; Cl, 27.92; S, 6.31. Found: C, 44.80; H, 5.37; N, 8.15; Cl, 27.70; S, 6.49.

EXAMPLE 63

1000 tablets each containing the following ingredients:

| | |
|---|---|
| 1,4-Dihydro-6-methyl-4-(3-nitrophenyl)-2-(2-propenylthio)-5-pyrimidinecarboxylic acid, ethyl ester | 100 mg. |
| Cornstarch | 50 mg. |
| Gelatin | 7.5 mg. |
| Avicel (microcrystalline cellulose) | 25 mg. |
| Magnesium stearate | 2.5 mg. |
| | 185 mg. | are prepared from sufficient bulk quantitied by mixing the 1,4-dihydro-6-methyl-4-(3-nitrophenyl)-2-(2-propenylthio)-5-pyrimidinecarboxylic acid, ethyl ester and cornstarch with an aqueous solution of the gelatin. The mixture is dried and ground to a fine powder. The Avicel and then the magnesium stearate are admixed with granulation. This mixture is then compressed in a tablet press to form 1000 tablets each containing 100 mg. of active ingredient.

In a similar manner, tablets containing 100 mg. of the product of any of Examples 1, 2, and 4 to 62 can be prepared.

A similar procedure can be employed to form tablets containing 50 mg. of active ingredient.

EXAMPLE 64

Two piece #1 gelatin capsules are filled with a mixture of the following ingredients:

| | |
|---|---|
| 1,4-Dihydro-6-methyl-2-(methylthio)-4-(2-nitrophenyl)-5-pyrimidinecarboxylic acid, ethyl ester, monohydrochloride | 50 mg. |
| Magnesium stearate | 7 mg. |
| Lactose | 193 mg. |
| | 250 mg. |

In a similar manner capsules containing 50 mg. of the product of any of Examples 1 to 31 and 33 to 62 can be prepared.

EXAMPLE 65

An injectable solution is prepared as follows:

| | |
|---|---|
| 1,4-Dihydro-6-methyl-4-(3-nitrophenyl)-2-[(phenylmethyl)thio]-5-pyrimidinecarboxylic acid, ethyl ester | 500 g. |
| Methyl paraben | 5 g. |
| Propyl paraben | 1 g. |
| Sodium chloride | 25 g. |
| Water for injection | 5 l. |

The active substance, preservatives, and sodium chloride are dissolved in 3 liters of water for injection and then the volume is brought up to 5 liters. The solution is filtered through a sterile filter and aseptically filled into presterilized vials which are closed with presterilized rubber closures. Each vial contains 5 ml. of solution in a concentration of 100 mg. of active ingredient per ml. of solution for injection.

In a similar manner, an injectable solution containing 100 mg. of active ingredient per ml. of solution can be prepared for the product of any of Examples 2 to 62.

EXAMPLE 66

1000 tablets each containing the following ingredients:

| | |
|---|---|
| 1,4-Dihydro-6-methyl-4-(3-nitrophenyl)-2-(2-propenylthio)-5-pyrimidinecarboxylic acid, ethyl ester | 100 mg. |
| Avicel | 100 mg. |
| Hydrochlorothiazide | 12.5 mg. |
| Lactose | 113 mg. |
| Cornstarch | 17.5 mg. |
| Stearic acid | 7 mg. |
| | 350 mg. | are prepared from sufficient bulk quantities by slugging the 1,4-dihydro-6-methyl-4-(3-nitrophenyl)-2-(2-propenylthio)-5-pyrimidinecarboxylic acid, ethyl ester, Avicel, and a portion of the stearic acid. The slugs are ground and passed through a #2 screen, then mixed with the hydrochlorothiazide, lactose, cornstarch, and remainder of the stearic acid. The mixture is compressed into 350 mg. capsule shaped tablets in a tablet press. The tablets are scored for dividing in half.

In similar manner, tablets can be prepared containing 100 mg. of the product of any of Examples 1,2, and 4 to 62.

What is claimed is:
1. A compound of the formula

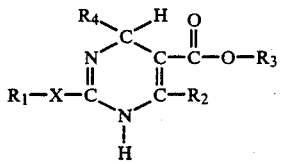

its 3,4-dihydropyrimidine tautomer form, or a pharmaceutically acceptable salt thereof wherein:

X is oxygen or sulfur;

$R_1$ is lower alkyl, lower alkenyl, lower alkynyl, —$(CH_2)_m$-cycloalkyl, —$(CH_2)_m$-aryl, —$(CH_2)_p$—OH, —$(CH_2)_p$—O—lower alkyl, —$(CH_2)_p$—O—$(CH_2)_m$-aryl, —$(CH_2)_p$—SH, —$(CH_2)_p$—S—lower alkyl, —$(CH_2)_p$—S—$(CH_2)_m$-aryl,

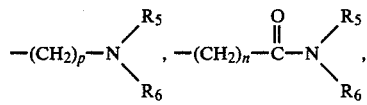

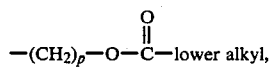

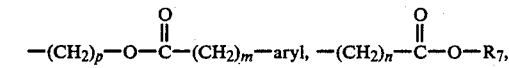

or halo substituted lower alkyl;

$R_2$ is hydrogen, lower alkyl, lower alkenyl, lower alkynyl, —$(CH_2)_m$—cycloalkyl, —$(CH_2)_m$—aryl, —$(CH_2)_n$—OH, —$(CH_2)_n$—O—lower alkyl, —$(CH_2)_n$—O—$(CH_2)_m$-aryl, —$(CH_2)_n$—SH, —$(CH_2)_n$—S—lower alkyl, —$(CH_2)_n$—S—$(CH_2)_m$—aryl,

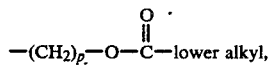

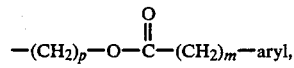

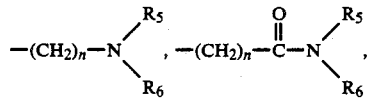

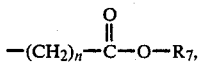

or halo substituted lower alkyl;

$R_3$ is hydrogen, lower alkyl, —$(CH_2)_m$—aryl, —$(CH_2)_m$—cycloalkyl, —$(CH_2)_p$—OH, —$(CH_2)_p$—O—lower alkyl, —$(CH_2)_p$—O—$(CH_2)_m$—aryl, —$(CH_2)_p$—SH, —$(CH_2)_p$—S—lower alkyl, —$(CH_2)_p$—S—$(CH_2)_m$—aryl,

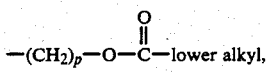

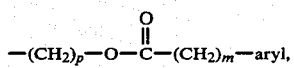

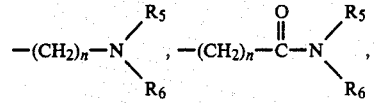

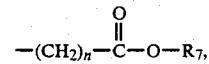

halo substituted lower alkyl, or a pharmaceutically acceptable salt forming ion;

$R_4$ is aryl;

$R_5$ and $R_6$ are independently selected from the group consisting of hydrogen, lower alkyl, and —$(CH_2)_m$—aryl or $R_5$ and $R_6$ taken together with the N atom to which they are attached complete a heterocyclic ring of the formula

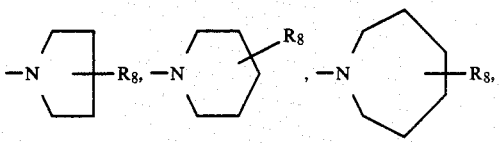

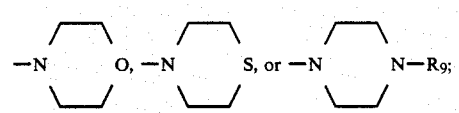

$R_8$ is hydrogen, lower alkyl of 1 to 4 carbons, lower alkoxy of 1 to 4 carbons, lower alkylthio of 1 to 4 carbons, halo, $CF_3$, or hydroxy;

$R_9$ is hydrogen, lower alkyl of 1 to 4 carbons,

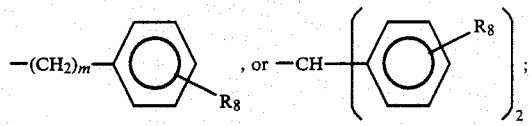

$R_7$ is hydrogen, lower alkyl, —$(CH_2)_m$—aryl, or a pharmaceutically acceptable salt forming ion;

m is zero or an integer from 1 to 6;

n is an integer from 1 to 6;

p is an integer from 2 to 6;

the term "lower alkyl" refers to straight or branched chain saturated hydrocarbon radicals of one to eight carbons;

the term "lower alkenyl" refers to straight or branched chain hydrocarbon radicals of two to eight carbons saturated except for one double bond;

the term "lower alkynyl" refers to straight or branched chain hydrocarbon radicals of two to eight carbons saturated except for one triple bond;

the term "cycloalkyl" refers to saturated carbocyclic rings of 4 to 7 carbons;

the term "halo" refers to chloro, bromo, and fluoro; and the term "aryl" refers to phenyl, 1-naphthyl, 2-naphthyl, mono substituted phenyl, 1-naphthyl or 2-naphthyl wherein said substituent is lower alkyl of 1 to 4 carbons, lower alkoxy of 1 to 4 carbons, lower alkylthio of 1 to 4 carbons, halo, nitro, cyano, hydroxy, amino, —NH—alkyl wherein alkyl is of 1 to 4 carbons, —N(alkyl)$_2$ wherein alkyl is of 1 to 4 carbons, CF$_3$, NCS, OCHF$_2$,

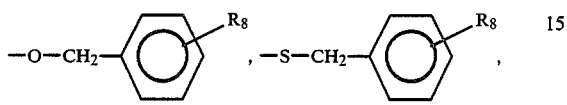

—O—CH$_2$—cycloalkyl, or —S—CH$_2$cycloalkyl, and di-substituted phenyl, 1-naphthyl, or 2-naphthyl wherein said substituents are selected from the group consisting of methyl, methoxy, methylthio, halo, CF$_3$, nitro, amino, and OCHF$_2$.

2. A compound of claim 24 wherein:
R$_1$ is lower alkyl of 1 to 5 carbons, lower alkenyl of 3 to 5 carbons, benzyl, 4-methoxybenzyl, or

R$_2$ is lower alkyl of 1 to 5 carbons;
R$_3$ is lower alkyl of 1 to 5 carbons, —(CH$_2$)$_p$—O—lower alkyl wherein lower alkyl is of 1 to 5 carbons,

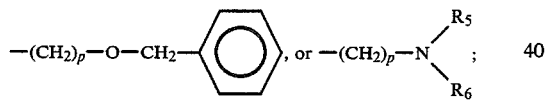

p is 2,3, or 4;
R$_4$ is phenyl, mono substituted phenyl wherein said substituent is at the 2- or 3- position and is lower alkyl of 1 to 4 carbons, lower alkoxy of 1 to 4 carbons, lower alkylthio of 1 to 4 carbons, halo, CF$_3$, nitro, or OCHF$_2$, or di substituted phenyl wherein said substituents are at the 2- and 3- positions and are selected from the group consisting of methyl, methoxy, methylthio, halo, CF$_3$, nitro, and OCHF$_2$; and
R$_5$ and R$_6$ are independently selected from the group consisting of hydrogen, lower alkyl of 1 to 5 carbons, and benzyl.

3. A compound of claim 2 wherein:
R$_2$ is methyl.

4. A compound of claim 3 wherein:
R$_1$ is methyl, pentyl, 2-propenyl, benzyl, 4-methoxybenzyl, or

R$_3$ is methyl, ethyl, isopropyl, or

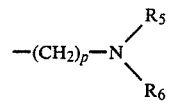

p is 2 or 3;
R$_5$ is methyl; and
R$_6$ is methyl or benzyl.

5. The compound of claim 4 wherein
X is oxygen;
R$_1$ is methyl;
R$_3$ is ethyl; and
R$_4$ is 3-nitrophenyl.

6. A compound of the formula

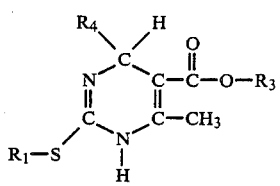

, its 3,4-dihydropyrimidine tautomer form, or a pharmaceutically acceptable salt thereof wherein:
R$_1$ is methyl, pentyl, 2-propenyl, benzyl, 4-methoxybenzyl, or

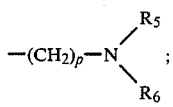

R$_3$ is ethyl, isopropyl, or

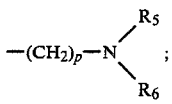

p is 2 or 3;
R$_4$ is 2-nitrophenyl, 3-nitrophenyl, 2-(trifluoromethyl)phenyl, or 2,3-dichlorophenyl;
R$_5$ is methyl; and
R$_6$ is methyl or benzyl.

7. A compound of claim 6 wherein:
R$_1$ is 2-propenyl or

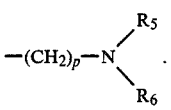

8. The compound of claim 7 wherein:
R$_1$ is 2-propenyl;
R$_3$ is ethyl; and
R$_4$ is 3-nitrophenyl.

9. The compound of claim 7 wherein:
R$_1$ is 2-propenyl;
R$_3$ is isopropyl; and
R$_4$ is 2,3-dichlorophenyl.

10. The compound of claim 7 wherein:
R$_1$ is

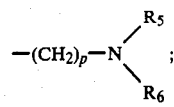

p is 3;
R₃ is isopropyl;
R₄ is 2,3-dichlorophenyl;
R₅ is methyl; and
R₆ is benzyl.
11. The compound of claim 7 wherein:
R₁ is

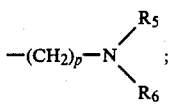

p is 2;
R₃ is isopropyl;
R₄ is 2,3-dichlorophenyl; and
R₅ and R₆ are both methyl.
12. The compound of claim 6 wherein
R₁ is benzyl;
R₃ is ethyl; and
R₄ is 3-nitrophenyl.
13. The compound of claim 6 wherein
R₁ is methyl;
R₃ is ethyl; and
R₄ is 3-nitrophenyl.
14. The compound of claim 6 wherein
R₁ is pentyl;
R₃ is ethyl; and
R₄ is 3-nitrophenyl.
15. The compound of claim 6 wherein
R₁ is methyl;
R₃ is ethyl; and
R₄ is 2,3-dichlorophenyl.
16. The compound of claim 6 wherein
R₁ is methyl;
R₃ is ethyl; and
R₄ is 2-nitrophenyl.
17. The compound of claim 6 wherein:
R₁ is methyl;
R₃ is ethyl; and
R₄ is 2-(trifluoromethyl)phenyl.
18. The compound of claim 6 wherein:
R₁ is methyl;
R₃ is

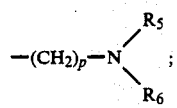

p is 2;
R₄ is 2-(trifluoromethyl)phenyl;
R₅ is methyl; and
R₆ is benzyl.
19. The compound of claim 6 wherein:
R₁ is 4-methoxybenzyl;
R₃ is isopropyl; and
R₄ is 2,3-dichlorophenyl.
20. The compound of claim 4 wherein
X is sulfur;
R₁ is 4-methoxybenzyl;
R₃ is ethyl; and
R₄ is 3-methylphenyl.
21. The compound of claim 4 wherein:
X is sulfur;
R₁ is 4-methoxybenzyl;
R₃ is methyl; and
R₄ is 3-nitrophenyl.
22. A composition useful in reducing blood pressure in a mammal comprising a pharmaceutically acceptable carrier and an anti-hypertensively effective amount of a compound or pharmaceutically acceptable salt thereof of the formula

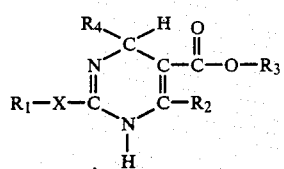

wherein X, R₁, R₂, R₃, and R₄ are as defined in claim 1.
23. The method of reducing blood pressure in a mammal comprising to a hypertensive mammal an effective amount of the composition of claim 22.

* * * * *